US00PP35808P2

(12) United States Plant Patent
Bean et al.

(10) Patent No.: US PP35,808 P2
(45) Date of Patent: May 14, 2024

(54) ***AGAPANTHUS* PLANT NAMED 'DWAGHYB05'**

(50) Latin Name: ***Agapanthus* hybrid**
Varietal Denomination: DWAgHyb05

(71) Applicant: De Wet Plant Breeders, Johannesburg (ZA)

(72) Inventors: Quinton Bean, Northriding (ZA); Charles Andrew De Wet, Sandton (ZA)

(73) Assignee: De Wet Plant Breeders, Johannesburg (ZA)

( * ) Notice: Subject to any disclaimer, the term of this patent is extended or adjusted under 35 U.S.C. 154(b) by 0 days.

(21) Appl. No.: 18/219,515

(22) Filed: Jul. 7, 2023

(30) Foreign Application Priority Data

May 4, 2023 (QZ) ..... PBR 20230971

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Penny J. Aguirre

(57) ABSTRACT

A new cultivar of *Agapanthus* plant named 'DWAgHyb05' that is characterized by its good resistance to root rot and crown rot, its bi-color flowers (white and purple), its long flowering period with a re-blooming habit, its fast growth habit with blooms at a young age, its compact plant habit and medium plant height, its high flower count per umbel, and its numerous inflorescences.

3 Drawing Sheets

Botanical classification: *Agapanthus* hybrid.
Varietal denomination: 'DWAgHyb05'.

CROSS REFERENCE TO RELATED APPLICATIONS

This application is related to a European plant breeders' rights application, Application No. 2023/0971 filed on May 4, 2023, under 35 U.S.C. 119(f), the entire contents of which is incorporated by reference herein. The information for the plant breeders' rights application was received directly from the Inventors. This application is also co-pending with U.S. Plant Patent Applications filed for plants derived from the same breeding program that are entitled *Agapanthus* Plant Named 'DWAgHyb01' (U.S. Plant patent application Ser. No. 18/112,983) and *Agapanthus* Plant Named 'DWAgHyb02' (U.S. Plant patent application Ser. No. 18/112,907).

BACKGROUND OF THE INVENTION

The present invention relates to a new and distinct cultivar of *Agapanthus* of hybrid origin and will be referred to hereafter by its cultivar name, 'DWAgHyb05'. 'DWAgHyb05' represents a new perennial grown for landscape and container use.

The new cultivar was derived from a controlled breeding program by the Inventors in Hartbeespoort, North West Province, South Africa. The goal of the breeding program was to develop a new cultivar of *Agapanthus* that re-blooms, has bi-color flowers, has a compact to medium-sized plant habit, and has resistant to rot caused by *Erwinia* sp. The Inventors made a cross in October of 2015 between unnamed and unpatented proprietary plants of *Agapanthus* from the Inventors' breeding program as both the female and male parents. The Inventors selected 'DWAgHyb05' in October of 2017 as a single unique plant amongst the seedlings that resulted from the above cross.

Asexual propagation of the new cultivar was first accomplished by division by one of the Inventors in Hartbeespoort, North West Province, South Africa in October of 2017. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'DWAgHyb05' as a distinct cultivar of *Agapanthus*.

1. 'DWAgHyb05' exhibits good resistance to root rot and crown rot.
2. 'DWAgHyb05' exhibits bi-color flowers (white and purple).
3. 'DWAgHyb05' exhibits a long flowering period with a re-blooming habit.
4. 'DWAgHyb05' exhibits a fast growth habit with blooms at a young age.
5. 'DWAgHyb05' exhibits a compact plant habit and medium plant height.
6. 'DWAgHyb05' exhibits a high flower count per umbel (dense).
7. 'DWAgHyb05' exhibits numerous inflorescences.

The female parent of 'DWAgHyb05' differs from 'DWAgHyb05' in having an inferior reblooming habit. The male parent of 'DWAgHyb05' differs from 'DWAgHyb05' in having flowers with the bi-color less prominent and paler in color. 'DWAgHyb05' can be most closely compared to the

*Agapanthus* cultivars 'WP001' (U.S. Plant Pat. No. 27,357), and 'Ambic001' (U.S. Plant Pat. No. 25,519), 'DWAgHyb01', and 'DWAgHyb02'. 'WP001' is similar to 'DWAgHyb05' in being floriferous and re-blooming and having a compact plant habit but differs from 'DWAgHyb05' in having flowers that are all white in color. 'Ambic001' is similar to 'DWAgHyb05' in having bi-colored flowers. 'Ambic001' differs from 'DWAgHyb05' in having a slower growth habit, a slightly taller plant height and leaves that are more narrow in shape, and in lacking rebloom and an evergreen habit in warm climates. 'DWAgHyb01' and 'DWAgHyb02' are both similar to 'DWAgHyb05' in having medium plant heights, high flower counts per umbel, and good resistance to root and crown rot. 'DWAgHyb01' differs from 'DWAgHyb05' in having flowers that are blue in color. 'DWAgHyb02' differs from 'DWAgHyb05' in having flowers that are dark purple in color.

STATEMENT REGARDING PRIOR DISCLOSURES BY THE INVENTORS

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantago, Golden Valley Plants, Van Meuwen, Thompson & Morgan, Dobies, Ibmec blog and Visions.

BRIEF DESCRIPTION OF THE DRAWINGS

The accompanying color photographs illustrate the overall appearance and distinct characteristics of the new *Agapanthus*. The photographs were taken of plants about 2 years in age of 'DWAgHyb05' as grown outdoors in a 23-cm container in Linbro Park, Johannesburg, South Africa.

The photograph in FIG. 1 provides a side view of a plant of 'DWAgHyb05' in bloom.

Figure 1:
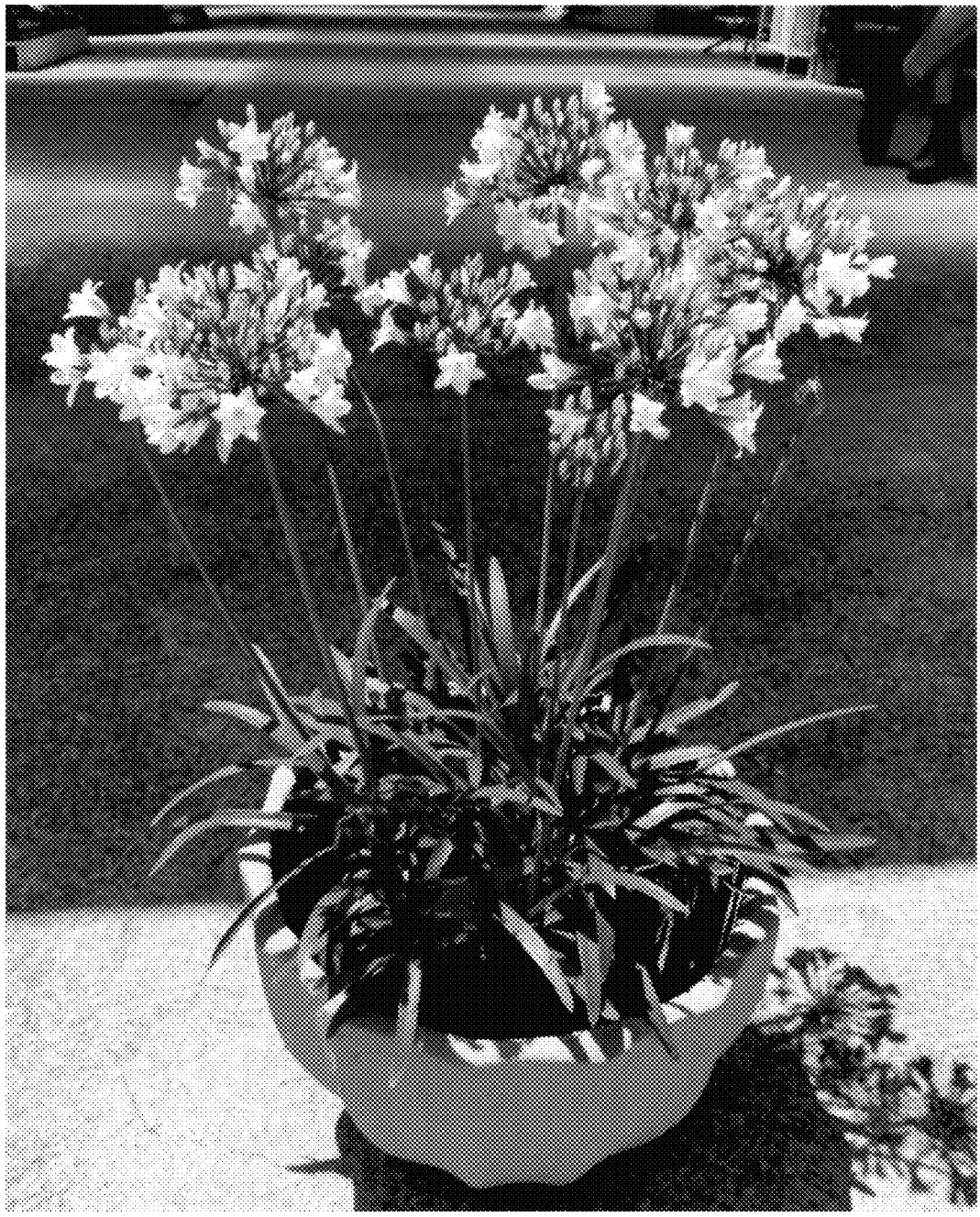
Figure 2:
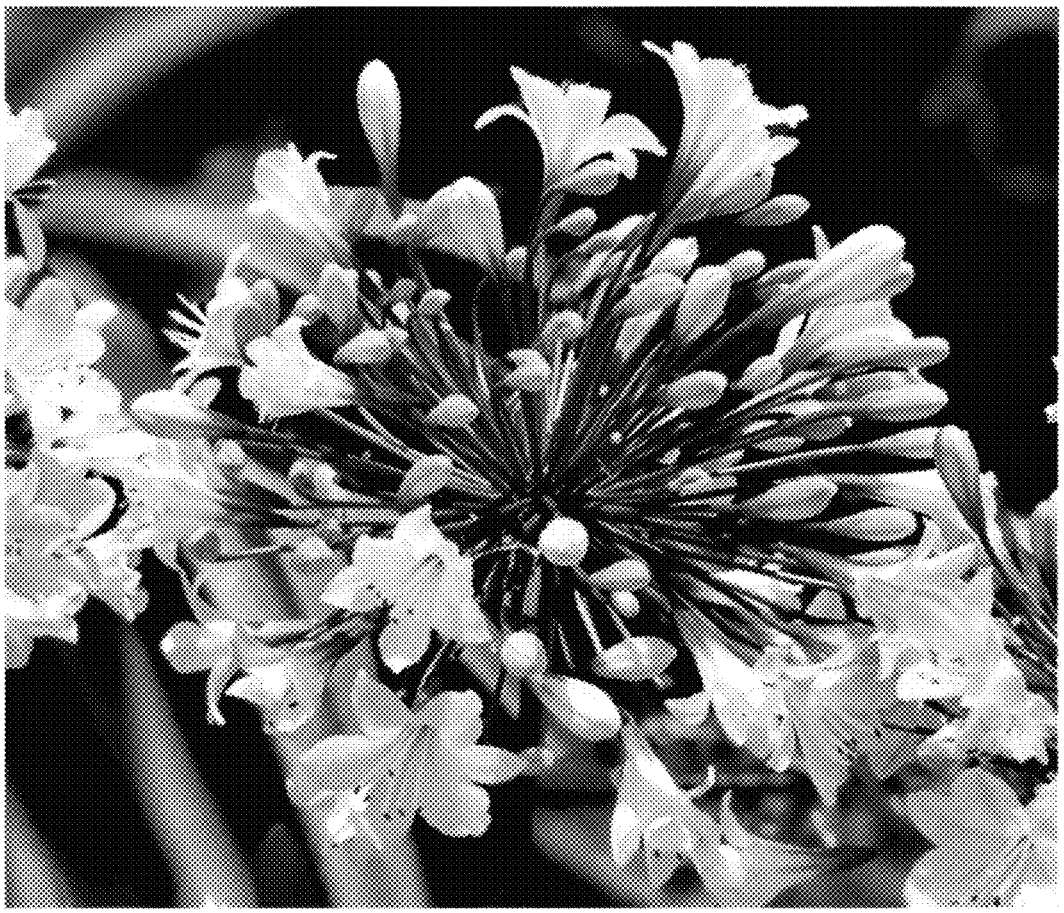

The photograph in FIG. 2 provides a close-up view of an inflorescence of 'DWAgHyb05'.

Figure 3:
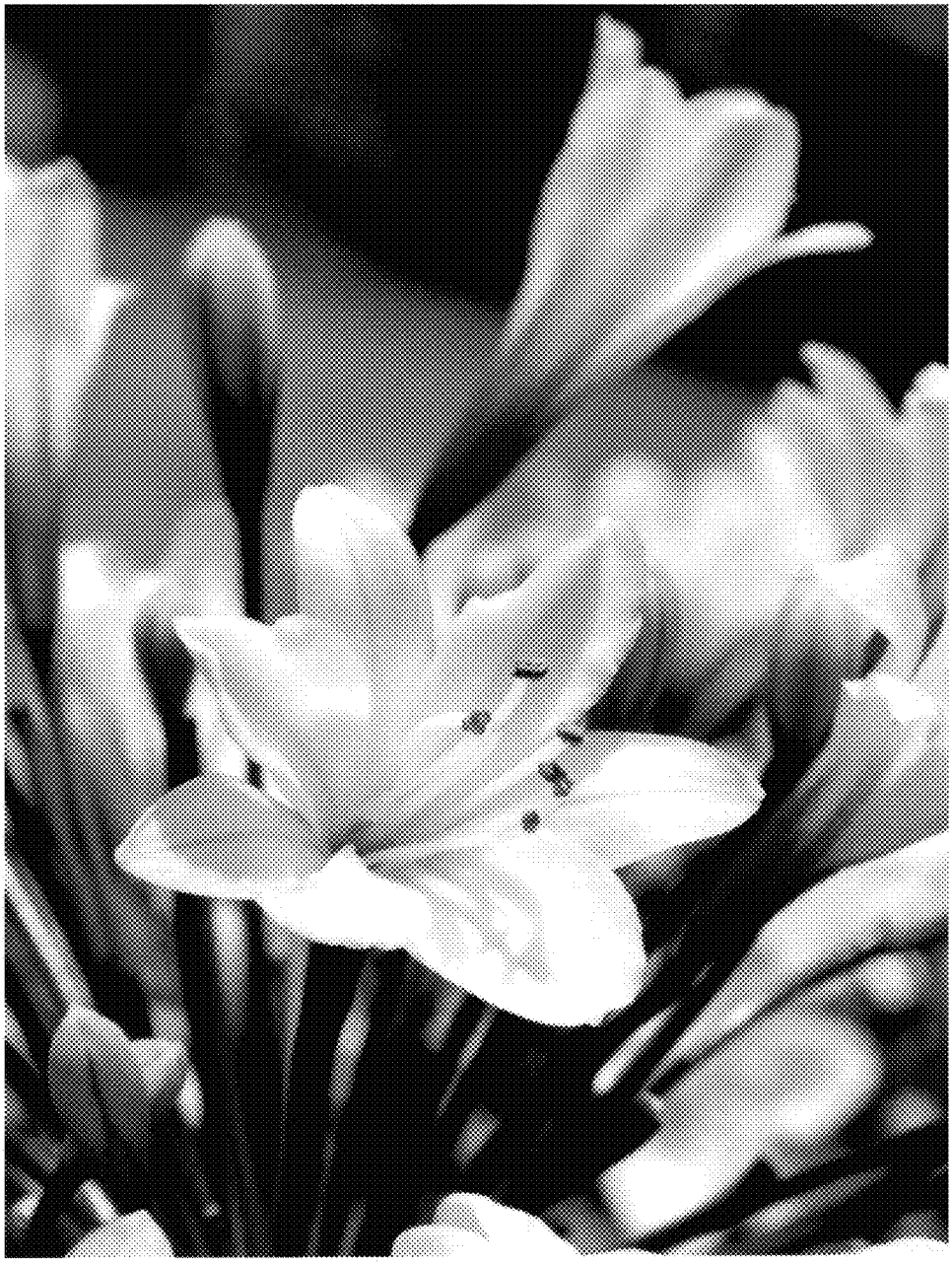

The photograph in FIG. 3 provides a close-up view of a flower of 'DWAgHyb05'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 3-year-old plants of 'DWAgHyb05' as grown outdoors in 23-cm containers in Beaulieu, The United Kingdom. The phenotype of the new cultivar may vary with variations in environmental, climatic, and cultural conditions, as it has not been tested under all possible environmental conditions. The color determinations are in accordance with the 2015 Colour Chart of The Royal Horticultural Society, London, England, except where general color terms of ordinary dictionary significance are used.

General description:

*Blooming period.*—Main bloom, early to mid-summer with rebloom into November in South Africa.

*Plant type.*—Herbaceous perennial, evergreen in South Africa however, it is most likely to be semi-evergreen in colder climates (has not been tested).

*Plant habit.*—Compact, basal rosettes with inflorescences emerging from the rosette center.

*Height and spread.*—Medium; 63 cm in height and spread as a 3-year-old plant grown in a container.

*Cold hardiness.*—At least to U.S.D.A. Zone 8.

*Diseases and pests.*—Good resistance has been observed to crown rot caused by *Fusarium* sp. and root rot caused by *Erwinia* sp., no resistance or susceptibility to pests has been observed.

*Root description.*—Thick and fleshy, 161C in color.

*Propagation.*—Tissue culture (preferred) and division.

*Growth rate.*—Vigorous.

*Number of shoots* (*rosettes*).—An average of 13.

Foliage description:

*Leaf shape.*—Ligulate.

*Leaf division.*—Simple.

*Leaf base.*—Truncate.

*Leaf arrangement.*—2-ranked, arranged in shoots an average of 1.7 cm diameter at base.

*Leaf apex.*—Narrow acute.

*Leaf aspect.*—Emerging leaves erect, then cascade.

*Leaf venation.*—Parallel, upper surface; 144A, lower surface; 143A.

*Leaf margins.*—Entire.

*Leaf size.*—Up to 27 cm in length and up to 2 cm in width.

*Leaf surface.*—Smooth, glabrous, and dull on upper and lower surface.

*Leaf number.*—Average of 8 leaves per rosette.

*Leaf color.*—Young leaves upper surface; 144B, leaves lower surface; 144B to 144C, mature leaves upper surface; 143A to 143B and 144B, mature leaves lower surface; 143B and 144B, anthocyanin at base of both surfaces is lacking.

*Leaf attachment.*—Sessile to base.

*Leaf density.*—Dense.

Flower description:

*Inflorescence type.*—Dense umbel.

*Flower fragrance.*—None.

*Flower type.*—Rotate, campanulate, base of tepals fused.

*Flower number.*—An average of 50 flowers per umbel.

*Inflorescence size.*—Average of 9 cm in height and 12 cm in diameter.

*Flower size.*—An average of 3.5 cm in depth and 4 cm in diameter.

*Lastingness of inflorescence.*—Average 7 days.

*Flower aspect.*—Upward, outward to downward.

*Peduncle.*—Very strong, oval in shape, held primarily upright, average of 58 cm in length and 1.7 cm in width, glabrous and slightly glaucous surface, satiny, color; young 144B to 144C, mature 143A to 143B, no anthocyanin present.

*Pedicels.*—Very strong, round in shape, aspect held in various angles, average of 3 cm in length and 1 mm in width, glabrous surface, color; 144C, tip 93A.

*Flower buds.*—Obelliptic in shape, average of 2.2 cm in length and 1.3 cm in width, color; a blend of NN155A and 144C to 144D, base 93B.

*Flower bract.*—Ovate to lanceolate in shape, acuminate apex, truncate base, up to 5 cm in length and 1.7 cm in width, color (both surfaces); 144B to 144C and becoming suffused with 93A to 93B as it matures, surface glabrous and dull, opens on one side.

*Tepals.*—6, oblanceolate in shape, entire to slightly undulate margins, apex of inner tepals rounded with slight notch, apex of outer tepals acute and slightly ruffled, both surfaces glabrous and satiny, moderately thick substance, an average of 2.5 cm in length and 1 cm in width, color; both surfaces N155D, base 93B to 93C.

Reproductive organs:

*Gynoecium.*—Pistil; 1, average of 2.5 cm in length, stigma; narrow clavate in shape and NN155D in color, style; 2.3 cm in length, NN155D in color, ovary; oblong in shape, 7 mm in length, 3 mm in width and 145C in color.

*Androecium.*—Stamens; 6, anthers; dorsifixed, extrusion medium, obcordate in shape, average of 2 mm in length, N92B in color, filament; 2.1 cm in length, N155D in color, pollen; moderate in quantity, 1A in color.

*Staminodes and pistillodes.*—Not present.

*Fruit/seed.*—Have not been observed to date.

It is claimed:

1. A new and distinct cultivar of *Agapanthus* plant named 'DWAgHyb05' as herein illustrated and described.

* * * * *